United States Patent
Somani

(10) Patent No.: US 7,575,322 B2
(45) Date of Patent: Aug. 18, 2009

(54) AUTO-ALIGNMENT AND AUTO-FOCUS SYSTEM AND METHOD

(75) Inventor: Seema Somani, Milpitas, CA (US)

(73) Assignee: AMO Development LLC., Santa Ana, CA (US)

(*) Notice: Subject to any disclaimer, the term of this patent is extended or adjusted under 35 U.S.C. 154(b) by 40 days.

(21) Appl. No.: 11/747,582

(22) Filed: May 11, 2007

(65) Prior Publication Data
US 2008/0278687 A1 Nov. 13, 2008

(51) Int. Cl.
A61B 3/14 (2006.01)
A61B 3/10 (2006.01)

(52) U.S. Cl. .................................. 351/208; 351/221

(58) Field of Classification Search .............. 351/200, 351/205–208, 210, 221
See application file for complete search history.

(56) References Cited

U.S. PATENT DOCUMENTS

| | | | |
|---|---|---|---|
| 5,071,245 A * | 12/1991 | Fukuma et al. | ............ 351/211 |
| 5,144,630 A | 9/1992 | Lin | |
| 5,210,554 A | 5/1993 | Cornsweet et al. | |
| 5,469,234 A | 11/1995 | Konishi | |
| 5,526,072 A | 6/1996 | El Hage | |
| 5,742,626 A | 4/1998 | Mead et al. | |
| 6,004,313 A | 12/1999 | Shimmick et al. | |
| 6,315,413 B1 | 11/2001 | Shimmick et al. | |
| 6,419,671 B1 | 7/2002 | Lemberg | |
| 6,460,997 B1 | 10/2002 | Frey et al. | |
| 6,520,958 B1 | 2/2003 | Shimmick et al. | |
| 6,550,917 B1 | 4/2003 | Neal et al. | |
| 6,598,975 B2 | 7/2003 | Liang et al. | |
| 6,634,750 B2 | 10/2003 | Neal et al. | |
| 2002/0110948 A1 | 8/2002 | Huang et al. | |
| 2003/0004500 A1 | 1/2003 | Clapham et al. | |
| 2004/0061830 A1 | 4/2004 | Hellmuth et al. | |
| 2005/0110948 A1 | 5/2005 | Bille | |
| 2005/0124983 A1 | 6/2005 | Frey et al. | |
| 2006/0061731 A1 | 3/2006 | Kuhn et al. | |
| 2007/0163049 A1 | 7/2007 | Brinkerhoff et al. | |
| 2007/0174971 A1 | 8/2007 | Brinkerhoff et al. | |

FOREIGN PATENT DOCUMENTS

| | | |
|---|---|---|
| EP | 0 659 382 | 6/1995 |
| WO | WO 02/46801 | 6/2002 |
| WO | 03/053228 | 7/2003 |

OTHER PUBLICATIONS

International Search Report and Written Opinion of PCT Application No. PCT/US2008/061660, dated Dec. 22, 2008 20 pages total.

* cited by examiner

*Primary Examiner*—Scott J Sugarman
*Assistant Examiner*—Dawayne A Pinkney

(57) ABSTRACT

A patient positioning system for use with a patient comprises an optical image sensor. The optical image sensor measures an optical image of a tissue structure of an eye of the patient. An image sensor support supports the image sensor. A patient support supports the patient. A linkage is coupled to the image sensor support with the patient support. A processor is coupled to the optical image sensor to determine a gradient of an illumination level of the optical tissue structure image. The processor is coupled to the linkage and configured to articulate the linkage so as to adjust a separation distance from the tissue structure to the image sensor in response to the gradient of the optical tissue structure image.

36 Claims, 12 Drawing Sheets

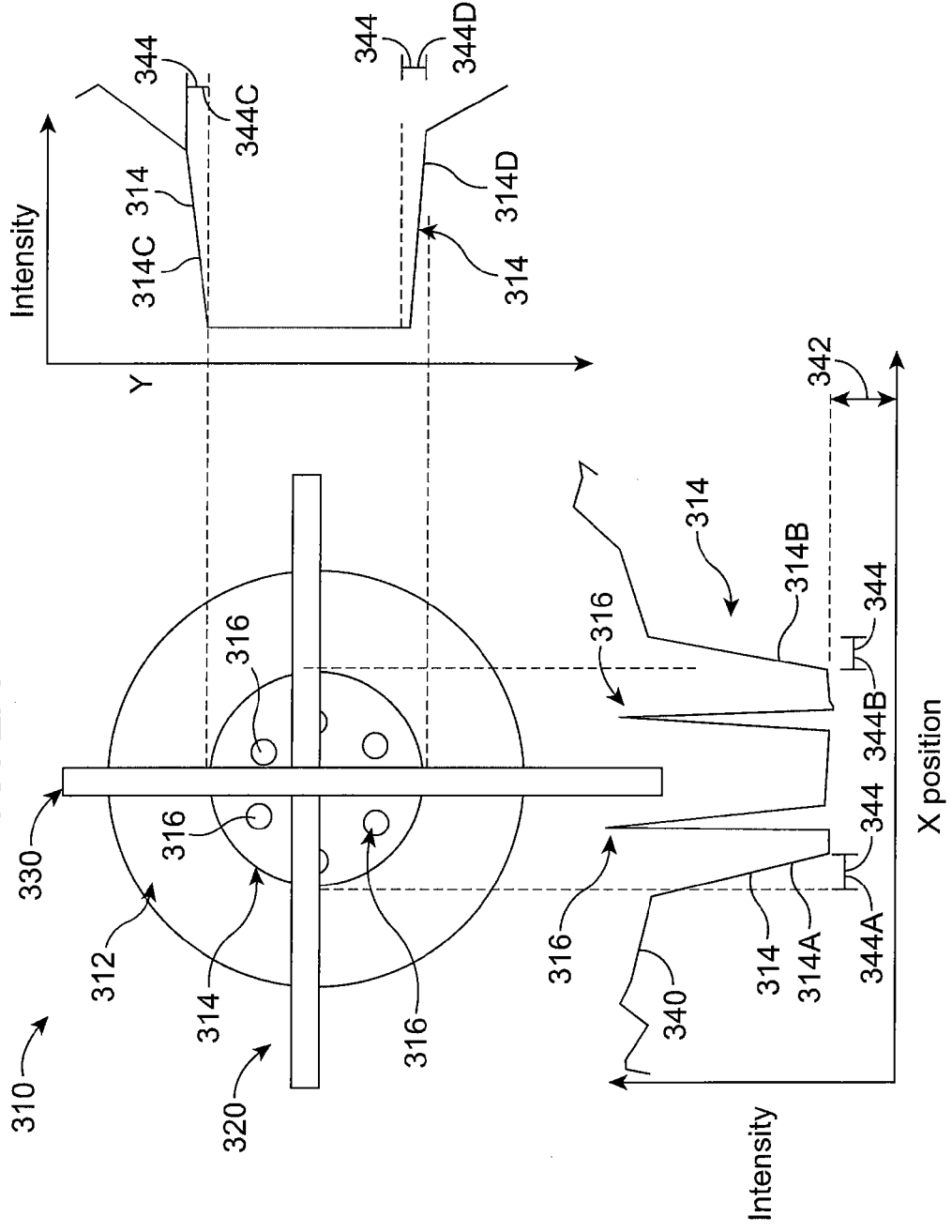

AUTO-ALIGNMENT AND AUTO-FOCUS SYSTEM AND METHOD

BACKGROUND OF THE INVENTION

The present invention relates generally to devices, systems, and methods for supporting and aligning patients with instruments and/or for analyzing ocular images. Exemplary embodiments of the present invention provide patient alignment between a support structure, such as a chin rest, chair, bed, or table, and a diagnostic instrument, such as a wavefront measurement device, in which the instrument can be moved into alignment with the patient. Other embodiments provide mechanisms for positioning the head and/or body of a patient to align the patient with an instrument during surgery.

Laser eye surgical procedures typically employ ultraviolet or infrared lasers to remove a microscopic layer of stromal tissue from the cornea to alter the cornea's refractive properties. Excimer laser systems generally use argon and fluorine gas to create a non-thermal laser light which can break molecular bonds in a process known as photoablation. Such systems result in the photodecomposition of the corneal tissue, but generally do not cause significant thermal damage to adjacent and underlying tissues of the eye. The photoablation removes the stromal tissue to change the shape or contour of the cornea and can be used to correct myopia (near-sightedness), hyperopia (far-sightedness), astigmatism, high-order aberrations, and the like.

Existing diagnostic systems can be used to measure optical errors of the eye and define a correction to eye. Many existing diagnostic measurement systems support the head of the patient with a chin rest and move the instrument into alignment while the head of the patient is supported with the chin rest. To align the patient with the diagnostic instrument, the instrument operator may adjust the height of the instrument, the separation distance from the instrument to the eye, and the lateral position of the instrument relative to the eye. In some instances, the patient may move while the patient is supported, such that alignment can be difficult in some instances.

Existing laser eye surgery systems have generally included an operator interface for use by the laser system operator in setting up, controlling, monitoring, and generally directing the laser treatment of the patient's eyes. Accurate photoablation of corneal tissues benefits from precise alignment between the eye and the therapeutic laser beam transmitted from the laser system. Many laser eye surgical alignment systems have a patient support that comprises a seat or bed so that the patient is treated while seated, while lying down, or while reclined in a supine position. To align the patient with the laser beam delivery optics, the system operator generally positions the seat or bed into alignment with the laser system. A particularly advantageous user interface and patient support system is described in U.S. patent application Ser. No. 10/226,867, entitled "Improved Interface for Laser Eye Surgery" as filed on Aug. 20, 2002, the full disclosure of which is incorporated herein by reference. Embodiments of that advantageous system may make use of a contoured patient treatment chair to help position a patient into nominal alignment with the laser, allowing the system operator to make fine adjustments using the system interface. As the system can be moved quickly to the nominal alignment for treatment of the left or right eyes, this improved interface system provides significant advantages in ease of use, overall procedure speed, and alignment accuracy. Another patient support system is described in U.S. patent application Ser. No. 11/335,177, as filed on Jan. 18, 2006, and entitled "Compression Head Pillow and Neck Angle Adjustment Mechanism for Refractive Laser Surgery and the Like", the full disclosure of which is incorporated herein by reference. Embodiments of that system may allow both the height of the patient's head and the angle of the patient's neck to be established independently, and/or may inhibit movement or deflection of the head of the patient from an aligned position.

While known patient support and alignment systems have allowed a large number of patients to benefit from the advantages of diagnostic measurements and laser eye surgery, still further improvements would be desirable. For example, it would be advantageous to more accurately position the patient into alignment with diagnostic instrument and/or laser system. It would also be advantageous to accommodate the wide range of patient physiologies, ideally without decreasing the speed or increasing the complexity of the alignment procedure. Preferably, these benefits would be provided without decreasing the system operator's access to the patient. At least some of these potential advantages may be realized by the systems, devices, and methods described herein below.

BRIEF SUMMARY OF THE INVENTION

The present invention generally provides improved devices, systems, and methods for supporting and positioning patients. Embodiments of the present invention provide an improved patient alignment between a support structure, such as a chin rest, chair, bed, or table, and a diagnostic instrument, such as a wavefront measurement device, in which the instrument can be moved into alignment with the patient. Other embodiments provide mechanisms for positioning the head and body of a patient to align the patient with an instrument during surgery. Embodiments of the present invention may be particularly useful for enhancing the speed, ease, safety, and efficacy of diagnostic eye measurements and laser eye surgical procedures such as photorefractive keratectomy ("PRK"), laser in situ keratomileusis ("LASIK"), and the like. Embodiments of a patient positioning system may include an image sensor to capture an image of a tissue structure of the eye, for example the boundary between the iris and pupil of the eye. A linkage may be coupled to a patient support and an image sensor support, such that the linkage can move the patient support and/or the image sensor support to align the image sensor with the patient. Gradients and/or slopes of illumination levels of the tissue structure can be determined, for example calculated with a processor. A separation distance from the image sensor to the tissue structure can be adjusted in response to the gradients and or slopes of the tissue structure in the image so as to bring the image of the tissue structure into focus. In some embodiments, the separation distance is adjusted so as to increase or maximize peaks of the gradients and/or to reduce or minimize widths of edges in the tissue structure image. A location of the pupil and/or iris in the image may be determined, and the linkage driven to align the pupil and/or iris with a predetermined location, for example a central position in the image.

In a first aspect, embodiments of the present invention provide a patient positioning system for use with a patient. The system comprises a patient support to position the patient. The patient has an eye with a tissue structure. An optical image sensor measures an optical image of the tissue structure. An optical train optically couples the positioned eye to the sensor so as to form the image of the tissue structure on the sensor. An optical path extends from the eye to the sensor. A processor is coupled to the optical image sensor to determine a gradient of an illumination level of the optical tissue structure image. The processor is configured to adjust at least one of the optical train or the patient support in response to the gradient so as to focus the image on the sensor.

In some embodiments, the optical train comprises at least one lens or mirror. The processors can be configured to adjust the lens or mirror to focus the image on the sensor. The illumination level may comprise a grey scale level.

In some embodiments, the optical tissue structure image may comprise a positive edge with a positive slope having a positive slope peak along the positive slope and a negative edge with a negative slope having a negative slope peak along the negative edge. The processor can be configured to determine a distance from the positive edge to the negative edge of the tissue structure image. The processor may be configured to determine the distance from the positive edge to the negative edge with the positive slope peak and the negative slope peak. The processor may be configured to reject at least one of the positive edge or the negative edge in response to the distance from the positive edge to the negative edge. The processor can be configured to reject at least one of the positive edge or the negative edge in response to the distance from the positive edge to the negative edge less than about 2.5 mm. The processor may be configured to smooth a portion of the tissue structure image in response to the distance from the positive edge to the negative edge. The processor can be configured to compare a magnitude of the positive slope peak to a threshold value, and use the positive slope peak to determine the gradient and location of the positive edge of the tissue structure image when the magnitude of the positive peak is above the threshold value. The processor may be configured to compare a magnitude of the negative slope peak to a threshold value and use the negative slope peak to determine the gradient and location of the negative edge of the tissue structure image when the magnitude of the negative peak is above the threshold value.

In some embodiments a patient positioning system for use with a patient is provided. The system may comprise an optical image sensor to measure an optical image of a tissue structure of an eye of the patient. An image sensor support supports the image sensor. A patient support supports the patient. A linkage couples the image sensor support to the patient support. A processor is coupled to the optical image sensor to determine a gradient of an illumination level of the optical tissue structure image. The processor is coupled to the linkage and configured to articulate the linkage so as to adjust a separation distance from the tissue structure to the image sensor in response to the gradient of the optical tissue structure image.

In some embodiments, the processor can be configured to increase or maximize the gradient of the tissue structure image with the separation distance from the tissue structure to the image sensor. The processor may be configured to determine a lateral location of the tissue structure in the image and to move the linkage laterally to position the tissue structure in response to the lateral location of the tissue structure in the image. The processor can be configured to determine the gradient of the tissue structure and the location of the tissue structure from the same image. The processor may be configured to move the linkage to adjust the separation distance and the location of the tissue structure at the same time.

In some embodiments, an optical axis extends between the tissue structure and the image sensor and the separation distance extends along the optical axis.

In some embodiments, the tissue structure of the optical image may comprise an iris with a pupil. An imaging lens may form an image of the tissue structure of the eye on the image sensor, and the imaging lens can be connected to the image sensor at a constant separation distance from the image sensor. The gradient may comprise a first gradient along a first dimension of a first region of the tissue structure image, and the processor may be configured to determine a second gradient along a second dimension of a second region of the tissue structure image. The processor can be configured to adjust a separation distance from the tissue structure to the image sensor in response to the first gradient and the second gradient of the tissue structure image. In specific embodiments, the first dimension is substantially perpendicular to the second dimension.

In some embodiments, the linkage can be adapted to move the image sensor support in response to the gradient of the tissue structure image. An imaging lens may form an image of the tissue structure of the eye on the image sensor, and the imaging lens can be connected to the image sensor to move with the image sensor at a constant separation distance from the image sensor.

In some embodiments, the linkage can move the patient support to adjust the separation distance in response to the gradient of the tissue structure image.

In some embodiments, a patient positioning system for aligning an instrument with an eye of a patient is provided. The system comprises an optical image sensor to capture an optical image of an iris of the eye of the patient. The iris may comprise a pupil, and the optical image may comprise pixels with intensity levels. An image sensor support can support the image sensor. A patient support may support the patient. A linkage may be coupled to the image sensor support with the patient support. A processor can be coupled to the optical image sensor to determine a pupil area of the image in response to intensity levels of the pixels within a range. The processor can be configured to determine slopes of the pixel intensity levels at the edge of the pupil. The processor may be coupled to the linkage and configured to articulate the linkage so as to adjust a separation distance from the tissue structure to the image sensor in response to the slopes of the pixel intensity levels at the edge of the pupil.

In some embodiments, the processor is configured to determine the slope with a width of the edge. The processor can be configured to determine a location of the pupil area in the image. The range may comprise a lower limit above zero and an upper limit that corresponds to estimated background levels of the pupil.

In another aspect, embodiments of the present invention provide, a method of aligning an instrument with an eye of a patient. The method comprises capturing an image of a tissue structure of the eye with an image sensor. The structure can comprise an edge, and the image may comprise pixels with illumination levels. A gradient of the tissue structure may be determined in response to the illumination levels of the pixels. An optical path from the tissue structure to the image sensor is adjusted in response to the gradient of the tissue structure.

The optical path can be adjusted in many ways. For example, the optical path can be adjusted with movement of at least one lens or mirror along the optical path. The optical path may be adjusted with at least one electro-optical lens or electro-optical mirror along the optical path. The optical path can be adjusted with movement of a patient support. The tissue structure may comprise an iris with a pupil and the processor can be configured to determine a location of the pupil in the image.

In some embodiments, a method of aligning an instrument with an eye of a patient is provided. The method comprises capturing an image of an iris of the eye with an image sensor. The iris may comprise a pupil, and the image may comprise pixels with intensity levels. An area of the pupil can be determined in response to the intensity levels of the pixels within a range. Slopes of the intensity levels can be determined at an edge of the pupil near the pupil area. An optical path from the iris to the image sensor can be adjusted in response to the slopes to increase the slopes at the edge of the pupil.

In specific embodiments, the separation distance can be adjusted to increase peak values of the slopes.

BRIEF DESCRIPTION OF THE DRAWINGS

FIG. 2A shows an image of an eye, according to embodiments of the present invention;

FIG. 2B shows an intensity profile along a horizontal section of the image of the eye as in FIG. 2A, according to embodiments of the present invention;

FIG. 2C shows an intensity profile along a vertical section of the image of the eye as in FIG. 2A, according to embodiments of the present invention;

DETAILED DESCRIPTION OF THE INVENTION

The present invention relates generally to devices, systems, and methods for supporting and positioning patients and/or for analyzing ocular images. Embodiments of the present invention provide an improved patient alignment between a support structure, such as a chin rest, chair, bed, or table, and a diagnostic instrument, such as a wavefront measurement device, in which the instrument can be moved into alignment with the patient. Other embodiments provide mechanisms for positioning the head and body of a patient and stabilizing the patient support, providing improved patient stability during surgery. Although specific reference is made to images of ocular tissue structures comprising an iris and a pupil of the eye, embodiments of the invention may used to image and focus on other ocular tissue structures, for example the limbus of the eye. Embodiments of the present invention may be particularly useful for enhancing the speed, ease, safety, and efficacy of diagnostic eye measurements and laser eye surgical procedures such as photorefractive keratectomy ("PRK"), laser in situ keratomileusis ("LASIK"), and the like.

Figure 1A:
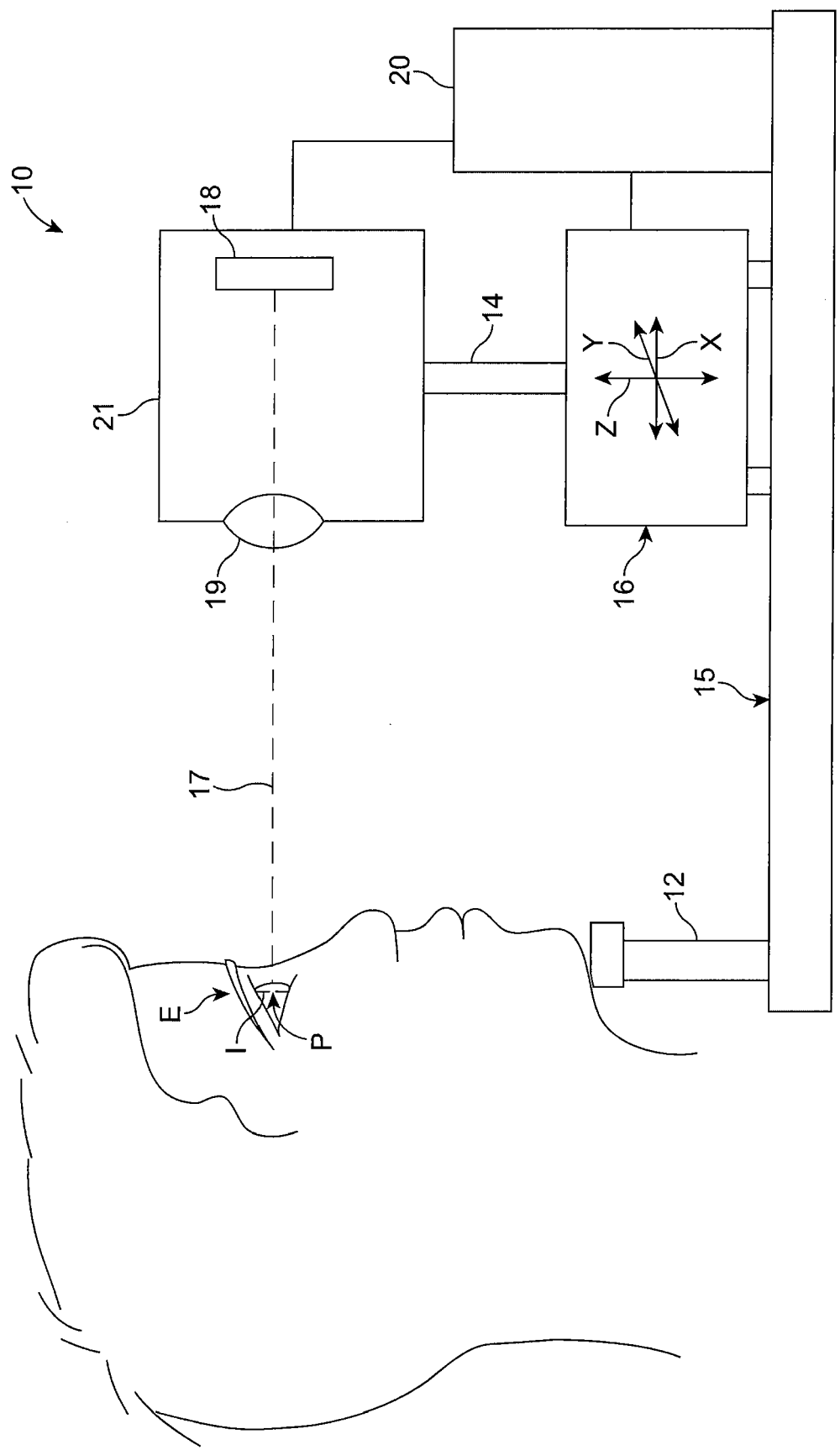
FIG. 1A shows an auto alignment and auto focus system, according to embodiments of the present invention.

Referring now to FIG. 1A, an auto alignment and auto focus system 10 is shown, according to embodiments of the present invention. System 10 includes a patient support 12 to support the head of a patient and thereby an eye E of the patient. Eye E comprises an Iris I with a pupil P. Patient support 12 may comprise many known methods of supporting a patient including chin rests, head rests beds, bite bars and the like. In some embodiments, a diagnostic instrument head 21 may comprises optical components and sensors to measure the eye. In some embodiments, diagnostic instrument 21 comprises an image sensor 18, for example a charge coupled device (CCD) array. A sensor support 14 may support diagnostic instrument head 21 and image sensor 18 with image sensor 18 attached to optics head 21. A table 15 supports patient support 12 and a linkage 16. Linkage 16, sensor support 14 and sensor 18 are connected to patient support 12 with table 15. Linkage 16 can move with independent translation in three dimensions, X, Y and Z, so as to move eye E and image sensor 18 in relation to each other. In some embodiments, linkage 16 supports image sensor 18 and moves image sensor 18 while patient support 12 remains stationary. In some embodiments, the linkage may support the patient support and move the patient with translation in three dimensions while the image sensor remains stationary.

A processor 20 can be connected to linkage 16 and image sensor 18 to control alignment of eye E relative to image sensor 18. An optical train comprising a lens 19 may be used to form an image of eye E on image sensor 18, for example an image of iris I and pupil P on image sensor 18. An optical axis 17 extends from eye E to image sensor 18, for example along dimension X. An optical path of light from eye E to sensor 18 includes a bundle of light rays that travel from eye E to sensor 18 along optical axis 17. In some embodiments, processor 20 controls linkage 16 to adjusts a physical separation distance between eye E and image sensor 18 along optical axis 17. In some embodiments, linkage 16 comprises motors that can be independently driven so as to move the support separately on each of the X, Y, and Z axes in response to commands from the processor. Although optical axis 17 may be straight and extend in a straight path from eye E to image sensor 18, the path of the optical axis may be curved with mirrors, prisms and the like. Processor 20 and/or linkage 16 may move image sensor 18 transverse to optical axis 17 to adjust a position of an image of eye E on image sensor 18, for example along a plane in the Y and Z dimensions. Linkages that can move an optics head of a diagnostic instrument with translational motion along three dimensions are described in U.S. Pat. No. 5,526,072, the full disclosures of which is incorporated herein by reference.

Image sensor 18, linkage 14 and computer 20 may be components of a diagnostic and/or laser eye surgery system and used to maintain relative alignment of the patient with the system. The image sensor 18 and other components of the system are aligned such that other components of the system, for example a Hartmann-Shack wavefront sensor, are aligned with the eye when the image sensor is aligned with the eye. In some embodiments image sensor 18 is comprised within a diagnostic ocular imaging system such as a corneal topography machine, an interferometer, an optical coherence tomography machine and/or a wavefront measurement system. Examples of eye measurement and surgery systems suitable for incorporation an alignment system in accordance with embodiments of the present invention include, the VISX Star S4 Excimer Laser System®, the LADAR Vision® system commercially available from Alcon of Forth Worth; Tex., the Zyoptix® Systems commercially available from Bausch & Lomb of Rochester N.Y.; the EC-5000 Series of excimer laser systems commercially available from NIDEK of Gamagori, Japan, the OPD Scan II also available from NIDEK; the MEL 80™ Excimer Laser and WASCA™ analyzer, both commercially available from Carl Zeiss Meditec, Inc. of Dublin, Calif., and the Wavescan Allegretto laser system with Tscherning aberrometer.

Wavefront systems collect and analyze light that is reflected off of the retina to determine the low order and high order aberrations (if any) that are present in the optical path of the patient's eye. Light will generally focus to a point in spherical waves through an eye that has no aberrations. However, light can distort when it passes through a refractive medium that has aberrations, such as an irregular cornea or lens. Wavefront sensors, such as Hartmann-Shack sensors, are capable of measuring the distortions in the wavefront as it exits the optical tissue of the eye.

Wavefront systems can segment each wavefront using a series of sub-apertures via holes or lenslets. In a lenslet-array based system, the light that travels through each sub-aperture and is focused onto an imaging device, such as a charge coupled device (CCD), using a series of lenslets corresponding to the sub-apertures. In a flat wavefront, the focal points are in line with the optical axes of the lenslets, and the resultant spot pattern matches the pattern of the sub-apertures. When the wavefront is distorted due to aberrations in the eye, each focal point will shift proportionate to the gradient of that part of the wave that passes through the corresponding lenslet. The resultant pattern will have an irregular form.

The wavefront data can be constructed into a color representation of visual acuity or wavefront variations over the entire surface area of the pupil. The map can precisely represent variations in refractive status encompassing the entire optical system, based on measurements taken of the wavefront as it exits the eye. Low order, higher-order, and spherocylindrical aberrations can be captured by wavefront systems, such as the VISX WaveScan®. System so as to allow the surgeon to make an objective assessment of the wavefront-based refraction. Additional details on imaging corneal profiles may be found in U.S. Pat. Nos. 6,315,413; 6,419,671; and 6,520,958, and in International Publication No. WO 02/46801, assigned to the assignee of the present invention and incorporated herein by reference for all purposes.

Figure 1B:
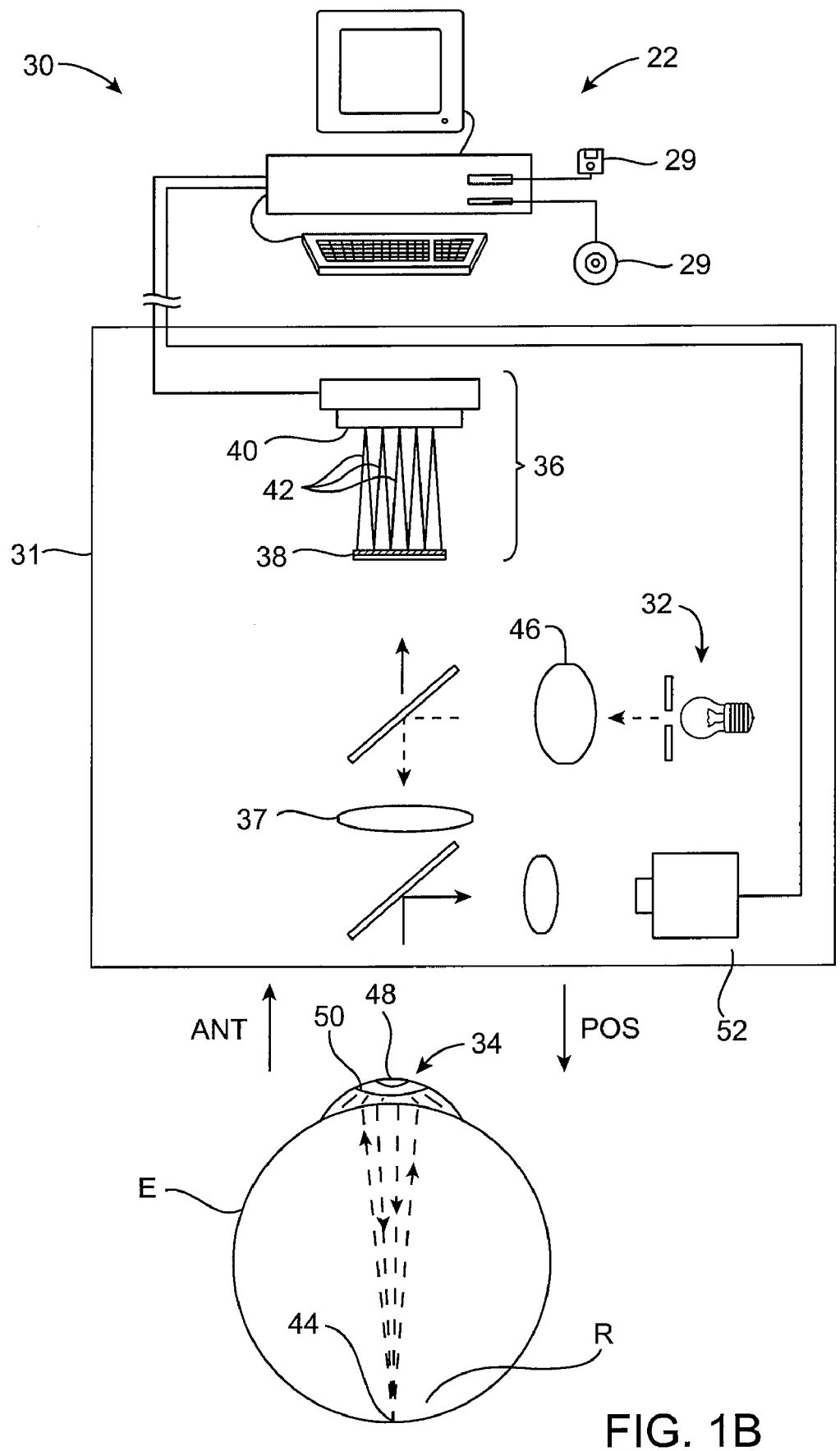
FIG. 1B schematically illustrates a method and system for directly determining a corneal ablation treatment prescription or program from wavefront sensor data, according to embodiments of the present invention.

Referring now to FIG. 1B, a wavefront sensor system 30 is schematically illustrated in simplified form, according to embodiments of the present invention. System 30 includes an optics head 31 that is supported with a linkage as described above. The linkage moves optics head 31 into alignment with eye E under control of a processor in response to images of the eye.

In very general terms, wavefront system 30 includes an image source 32 which projects a source image through optical tissues 34 of eye E and so as to form an image 44 upon a surface of retina R. The image from retina R is transmitted by the optical system of the eye (specifically, optical tissues 34), through one or more lens 37 as needed, and imaged onto a wavefront sensor 36 by system optics. The wavefront sensor 36 communicates signals to computer 22 for determination of a corneal ablation treatment program. Computer 22 may be the same computer which is used to direct operation of the laser surgery system 10, or at least some or all of the computer components of the wavefront sensor system and laser surgery system may be separate. Data from wavefront sensor 36 may be transmitted to a separate laser system computer via tangible media 29, via an I/O port, via an networking connection such as an intranet or the Internet, or the like.

Wavefront sensor 36 often comprises a lenslet array 38 and an image sensor 40. As the image from retina R is transmitted through optical tissues 34 and lenslet array 38, the lenslet array separates the transmitted image into an array of beamlets 42, and (in combination with other optical components of the system) images the separated beamlets on the surface of sensor 40. In some embodiments, sensor 40 comprises a charged couple device (CCD). Sensor 40 senses the characteristics of beamlets 42, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue. Additional characteristics of the spots may be used to determine the gradient of the associated region of optical tissue, for example the spot size and intensity.

Eye E generally defines an anterior orientation (ANT) and a posterior orientation (POS). Image source 32 generally projects an image in a posterior orientation through optical tissues 34 onto retina R. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics may decrease lower order optical errors by compensating for spherical and/or cylindrical errors of optical tissues 34. Higher order optical errors of the optical tissues may also be compensated through the use of an adaptive optic element, such as a deformable mirror. Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have well-defined and accurately formed image 44 on retina R.

While reference to sensing of an image 44 is described, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront sensor system 30 by focusing on a fixation target, as described in U.S. Pat. No. 6,004,313, the full disclosure of which is incorporated herein by reference. By varying a focal position of the fixation target as described in that reference, optical characteristics of the eye may be determined while the eye accommodates or adapts to image a field of view at a varying distance. Further alternatives include rotating the eye by providing alternative and/or moving fixation targets within wavefront sensor system 30.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 1C:
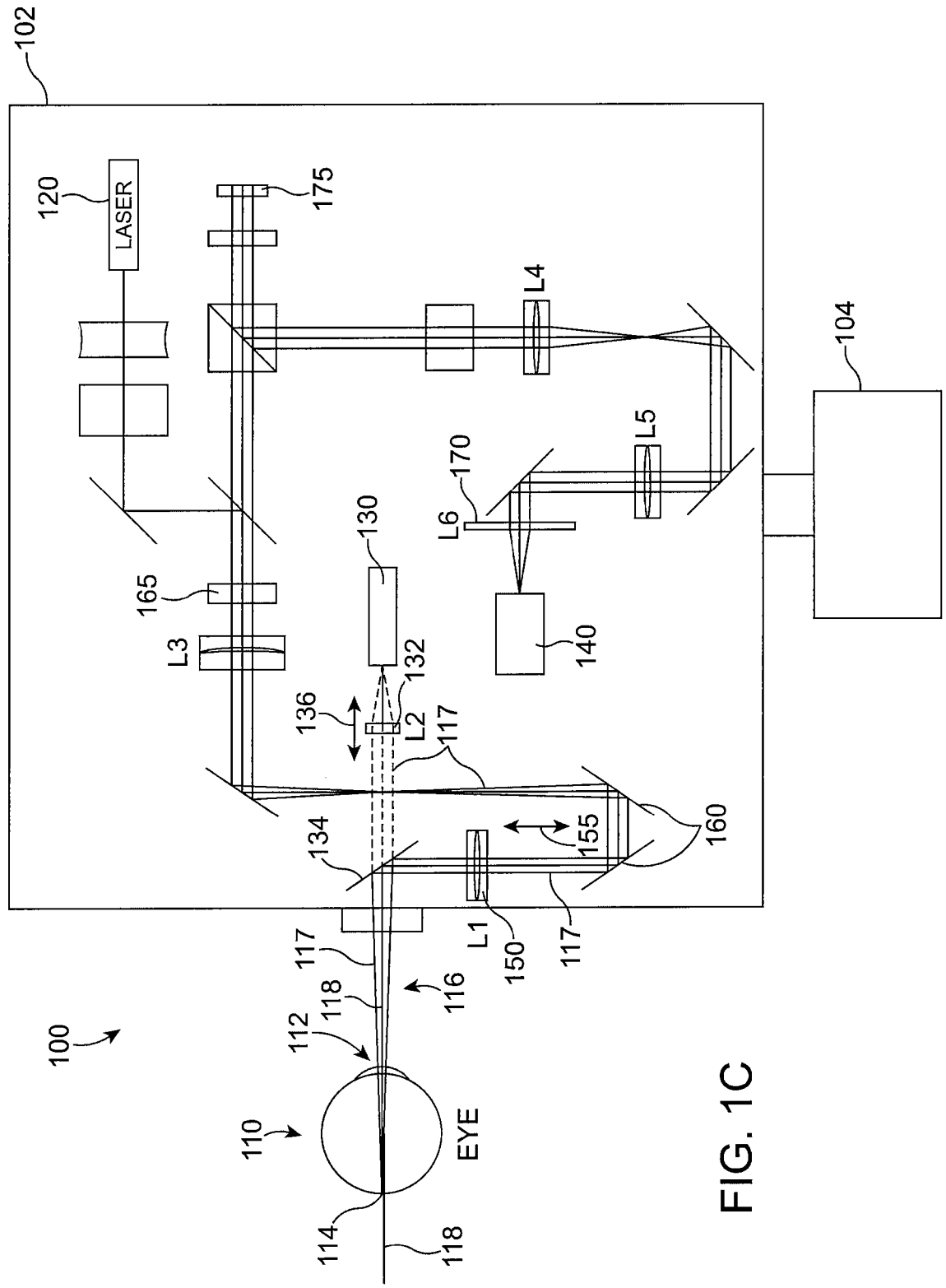
FIG. 1C schematically illustrates a method and system according to embodiments of the present invention for imaging a patient's eye.

Turning now to FIG. 1C, a system 100 of the present invention is shown, in accordance with embodiments of the present invention. As discussed in conjunction with FIG. 1B, system 100 may be used for imaging an eye 110 having a retina and may be operated in a similar manner as system 30. System 100 comprises an optics head 102 supported with a linkage 104. Linkage 104 can move optics head 102 into alignment with eye 110.

System 100 projects a light 116 or other image into and through optical tissues 112 of eye 110. Light 116 forms an image upon a surface 114 of the retina. Preferably, light 116 is transmitted into eye 110 along an optical axis 118. Light 116 travels along an optical path 117. Optical path 117 includes optical axis 118 and marginal rays disposed around the optical axis. System 100 comprises an optical train that includes several optical components such as lenses and mirrors that define optical path 117 and optically couple the eye with optical sensors of system 100. Optical sensors of system 100 include, for example, a pupil camera 130 and an imaging sensor 140, such as a CCD camera. The proper alignment between system 100 and optical tissues 112 may be facilitated by an image sensor, for example pupil camera 130. Similar to pupil camera 52, pupil camera 130 images the pupil to determine a position of the pupil for registration of the wavefront sensor data relative to the eye's optical tissues 112. A beam splitter 134 may be used to split optical path 117 into two or more components, such that optical path 117 extends from eye 110 to camera 130. A lens 132 may comprise several lens elements that form an image of the pupil on camera 130.

Lens 132 may be under computer control and adjust optical path 117 so as to focus the image of the tissue structure of the eye on the sensor in response to gradients of the image of the tissue structure and/or widths of features in the tissue structure image. In some embodiments, lens 132 is movable with an electromechanical mechanism and the position of the lens can be adjusted, as indicated by arrows 136. Lens 136 may comprise electro optical components such that the focus of the lens can be adjusted without moving the lens. The light or image source may include a laser 120, a bulb or directed light in the visible range, or some other illumination mechanism.

As shown schematically in FIG. 1C, system 100 includes a series of lenses and reflectors to direct the light or image into alignment with optical axis 118 and to or through various system 100 components. In some embodiments, the lenses include a lens 150 (L1) which is adapted to travel relative to reflectors 160 as shown by an arrow 155. Lens 150 can be adapted to compensate for large spherical aberrations of eye 110, for example with movement of lens 150 along optical path 117 such that the optical path is adjusted to compensate for spherical aberrations. In some embodiments, reflectors 160 may move as indicated by arrows 155 to adjust optical path 117, such that an optical distance from eye 110 to sensor 140 is adjusted, so as to compensate for spherical aberration. In some embodiments, a distance of optical path 117 from eye 110 to sensor 140 can be adjusted while a physical separation distance from eye 110 to sensor 140 remains constant, for example with movement of reflectors 160 as indicated by arrows 155. Further, system 100 may include an astigmatic lens 165 adapted to compensate for large irregularities in eye 110, such as astigmatism or other aberrations. In some embodiments, astigmatic lens 165 can be rotated to correspond with an axis of astigmatism of the eye. A mirror 175 can be provided along the optical path to reflect light. In some embodiments, mirror 175 may comprise electro-mechanical, electro-optical and/or micro-electro-mechanical systems (MEMS) to adjust optical path 117 extending from eye 110 to sensor 140.

In particular embodiments, light 116 exiting anteriorly from eye 110 is directed to a lenslet array 170 (L6) having a plurality of spaced-apart apertures. Lenslet array 170 may be similar to lenslet array 38 shown in FIG. 1B. Light 116 passes through lenslet array 170 and is received by imaging sensor 140, which in some embodiments is a Hartmann-Shack imaging sensor. Characteristics of light 116 imaged by sensor 140 can be used to determine the characteristics of an associated region of optical tissues 112. In some embodiments, optical path 117 can be adjusted with at least one of lens 150 and/or mirror 160 so as focus the spots on sensor 140 in conjunction with adjustments to optical path 117 that extends to camera 130 with lens 132. In some embodiments, mirror 175 may be under computer control to adjust optical path 117 in response to gradients of images comprising spots on sensor 140 and/or in response to gradients of tissue structure images on sensor 130.

In some embodiments, sensor 140 includes a CCD camera. In a particular embodiment, the CCD camera may have a dynamic range of about 69 dB. In some embodiments, light 116 transmitted anteriorly from eye 110, through system 100 to imaging sensor 140 produces a series of bright lights or spots against a generally dark background.

Figure 1D:
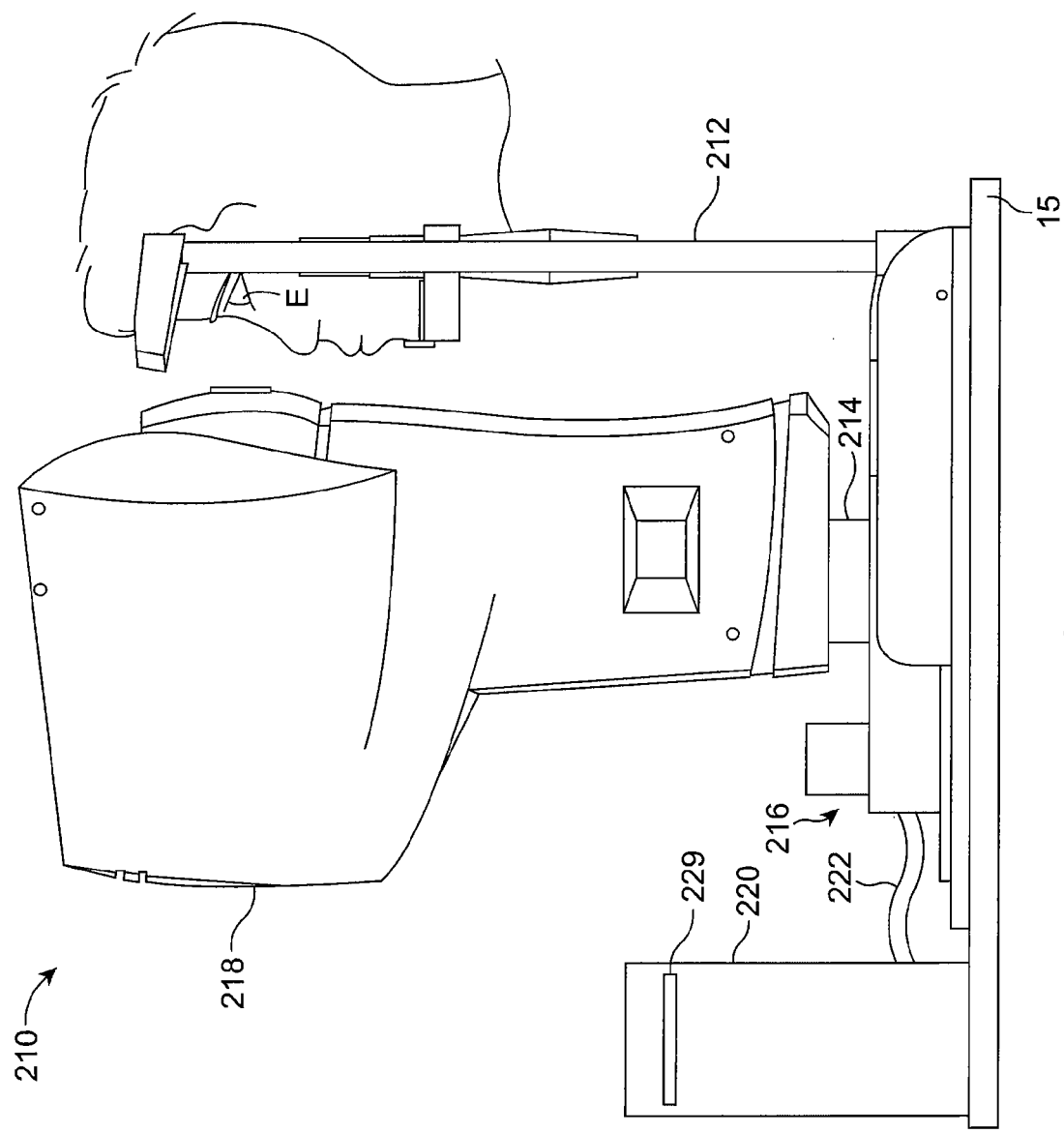
FIG. 1D schematically illustrates a diagnostic wavefront measurement system, according to embodiments of the present invention.

Referring now to FIG. 1D, a diagnostic wavefront measurement system 210 is schematically illustrated, according to embodiments of the present invention. Wavefront measurement system 210 includes a patient support 212 to support the patient and thereby support an eye E of the patient. Patient support 212 may comprise many known methods of supporting a patient including chin rests, bite bars and the like, while the patient is seated in front of the measurement device. In some embodiments, a diagnostic instrument head 218 comprises optical components and sensors to measure the eye, as described above. In some embodiments, diagnostic instrument head 318 comprises an image sensor, for example a charge coupled device (CCD) array that can be used to align the eye. A support 214 may support diagnostic instrument head 218. A table 215 supports patient support 212 and a motor driven linkage 216. Motor driven linkage 216, support 214 and instrument head 218 are connected to patient support 212 with table 215. Motor driven linkage 216 can move with independent translation in three dimensions, X, Y and Z, so as to move instrument head 218 in relation to eye E. A processor 220 comprising a tangible medium 229 can be connected to motor driven linkage 216 with a cable 222. Command signals from processor 220 can drive the linkage so as to align instrument head 218 with eye E of the patient. Processor 220 is capable of processing images of eye E in real-time and driving motor driven linkage 216 simultaneously in real-time so as to align eye E with diagnostic wavefront system 210. In some embodiments, diagnostic wavefront system 210 comprises a WaveScan® WaveFront System, available from VISX, Incorporated of Santa Clara, Calif.

Referring now to FIG. 2A, an image 310 of an eye is shown according to embodiments of the present invention. Image 310 may be obtained with a CCD camera in a wavefront system as described above. Image 310 comprises an iris 312 with a pupil edge 314, or boundary, that defines the pupil. LED reflections 316 are shown in the pupil. LED reflections 316 may result from LED's used to illuminate the iris of the eye and show noise that may be filtered from the image. Image 310 comprises a horizontal section 320 and vertical section 330. In some embodiments, image 310 comprises a gray scale image, although red, blue, and green color images may be used in some embodiments. In some embodiments, image sections can be taken at orientations besides 90 degree axes, for example sections along oblique angles.

Referring now to FIG. 2B, an intensity profile 340 along horizontal section 320 of image 310 of the eye as in FIG. 2A is shown, according to embodiments of the present invention. Intensity profile 340 comprises pupil edge 314 and LED reflections 316. A background level 342 corresponds to the dark region of the pupil. In some embodiments, background level 342 is within a range of values of estimated intensity levels for the pupil of the eye. Such estimated intensity levels can be obtained empirically with measurements from a patient population, for example measurements from 15 patients. A width 344 of pupil edge 314 corresponds to the focus of image 310.

Referring now to FIG. 2C, an intensity profile 350 along vertical section 330 of image 310 of the eye as in FIG. 2A is shown, according to embodiments of the present invention. Intensity profile 340 comprises pupil edge 314. Background level 342 corresponds to the dark region of the pupil. Width 344 of pupil edge 314 corresponds to the focus of image 310. In some embodiments, width 344 of pupil edge 314 can depend on the magnification and pixel resolution of the imaging sensor. One will recognize that many widths of pupil edge 314 can correspond to an in focus image of pupil edge 314, depending on the optical magnification and image sensor resolution.

In some embodiments, portions of pupil edge 344 can be analyzed and compared to determine tilt and aberration information. Along horizontal section 320, edge portion 314A includes a width 344A and edge portion 314B includes a width 344B. Along vertical section 330, edge portion 314C includes a width 344 C and edge portion 314D includes a width 344D. Each of the widths can be separately determined and compared to determine the tilt of the iris relative to the measurement instrument. In some embodiments, different widths along the same section indicate tilt of the iris, for example width 344A different from width 344B may indicate tilt of the iris along the horizontal axis. Additional sections at other angles can be taken to determine the exact angle and orientation of the iris tilt. In some embodiments, different focus for different sections may indicate aberrations of the cornea, for example astigmatism. With corneal astigmatism, the edge portions of the horizontal section may have similar widths and the edge portions of the vertical section may have similar widths and yet the widths of the horizontal and vertical sections may be different. Additional sections may be taken at several angles to determine the angle and magnitude of the astigmatism. In some embodiments, the processor can be configured to adjust the instrument and/or the patient obtain best focus for each portion of the edge of the iris, such that the best focus positions are measured and used to quantify tilt and/or aberrations. The processor may be configured to adjust the patient and/or the instrument in response to at least one of the tilt or the aberrations.

Figure 2D:
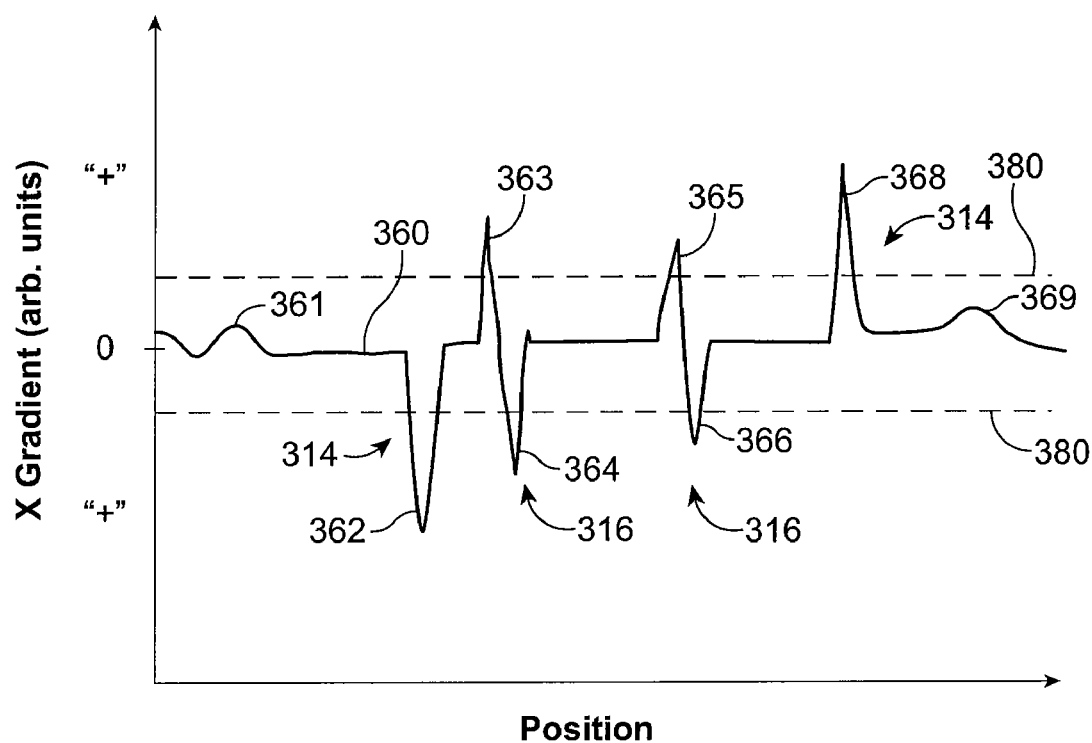
FIG. 2D shows gradients along the intensity profiles as in FIG. 2B, according to embodiments of the present invention.

Referring now to FIG. 2D, gradients are shown along the intensity profiles as in FIG. 2B, according to embodiments of the present invention. The gradient profiles can be determined by calculating the slope of the intensity profiles along each profile. A horizontal gradient profile 360 is shown along horizontal section 360. Horizontal gradient profile 360 can be calculated according to the equation $G_x = \Delta I/\Delta X$. where $G_x$ is the gradient along the horizontal X direction; $\Delta I$ is the change in illumination intensity between each pixel; and $\Delta X$ is the separation distance between each pixel along the horizontal dimension of the horizontal section. Horizontal gradient profile 360 comprises a negative peak 362 that corresponds to a first portion 314A of pupil edge 314 along the left side of the pupil edge, and a positive peak 368 that corresponds to a second portion 314B of pupil edge 314 along the right side of the pupil edge. The separation distance between the peaks can be used to determine a diameter of the pupil, and the positions of the pupil edge peaks can be used to determine the positions of the pupil. Horizontal gradient profile comprises a positive peak 363 in proximity to a negative peak 364 that corresponds to one of LED reflections 316, and a positive peak 365 in proximity to a negative peak 366 that corresponds to one of LED reflections 316.

Filters can be applied to the data to discriminate pupil edge boundaries from other image structures. For example the separation distance of the pupil edge peaks may correspond to an expected diameter of the pupil from about 2.5 to 7.5 mm. In some embodiments, any positive peak that is within about 2.5 mm of negative peak 362 can be rejected, and any positive peak that is more than about 7.5 mm from the negative peak can be rejected. Also, the gradient of the pupil comprises a negative edge followed by a positive edge that can be distinguished from the LED, as the LED reflections comprise a positive peak followed by a negative peak in close proximity, for example within about 1 mm.

A threshold 380 can be used to filter artifacts caused by noise and distinguish the edge of the pupil from other structures of the image. Gradient profile 360 comprises a peak 361 near the edge of the pupil. As the magnitude of peak 361 is below threshold 380, peak 361 can be excluded from analysis of pupil position. Although peak 362 and peak 363 have a magnitude greater than threshold 380, these peaks can be rejected based on separation distance as described above. In some embodiments, the magnitude of the gradient peaks may vary depending on the magnification and gain of the camera, and an autogain camera may be used.

Figure 2E:
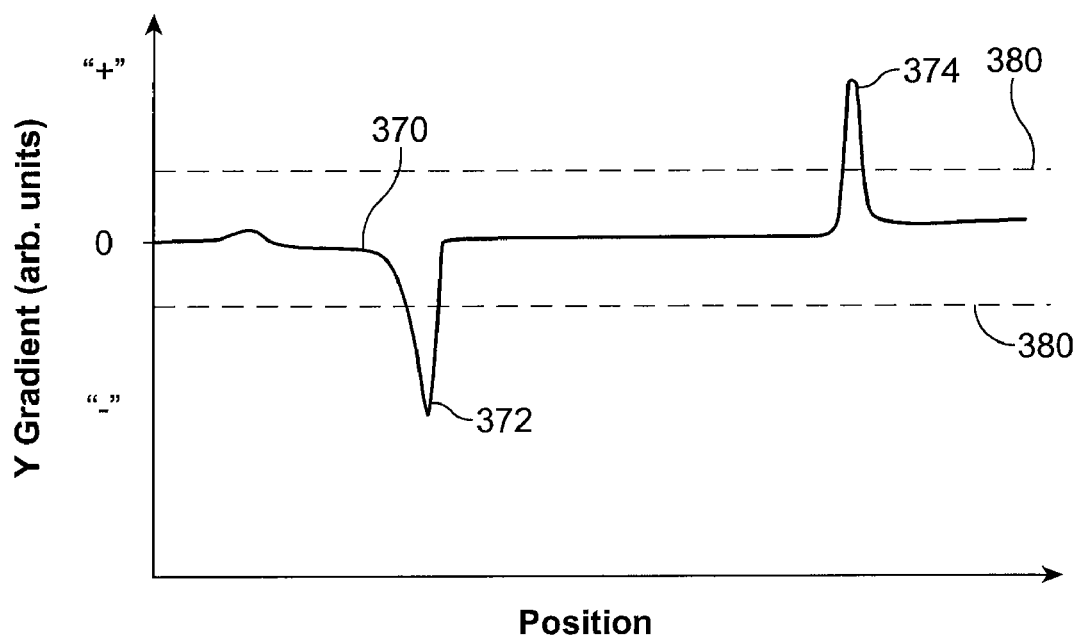
FIG. 2E shows gradients along the intensity profiles as in FIG. 2C, according to embodiments of the present invention.

Referring now to FIG. 2E, gradients are shown along the intensity profiles as in FIG. 2C, according to embodiments of the present invention. Vertical gradient profile 370 can be calculated according to the equation $G_y = \Delta I/\Delta Y$, where $G_y$ is the gradient along the vertical Y direction; $\Delta I$ is the change in illumination intensity between each pixel; and $\Delta Y$ is the separation distance between each pixel along the vertical dimension of the vertical section. Vertical gradient profile 370 comprises a negative peak 372, and a positive peak 374. Negative peak 372 corresponds to a negative edge of the pupil, and positive peak 368 corresponds to a positive edge of the pupil. Negative peak 372 and positive peak 374 have magnitudes above threshold 380, and a separated by at least 2.5 mm and no more than 7.5 mm, such that these peaks can be used to determine the diameter and location of the pupil.

In some embodiments, the eye and instrument are aligned in response to the position of the pupil on the image sensor so as to align the eye with an intended predetermined location of the image and/or image sensor. In some embodiments, the intersection of the horizontal row of pixels and vertical column of pixels corresponds to the predetermined location on the image. For example the intended aligned predetermined position of the eye may correspond to the center of the image. The pupil location can be determined in response to the above calculations along the image segments, for example the pupil center, and the linkage can move to align the pupil with the predetermined location of the image in response to the above calculations. For example, the processor can move the linkage horizontally to compensate for a horizontal error in the position of the center of the pupil, and the processor can move the linkage vertically to compensate for vertical error in the position of the image.

Figure 3A:
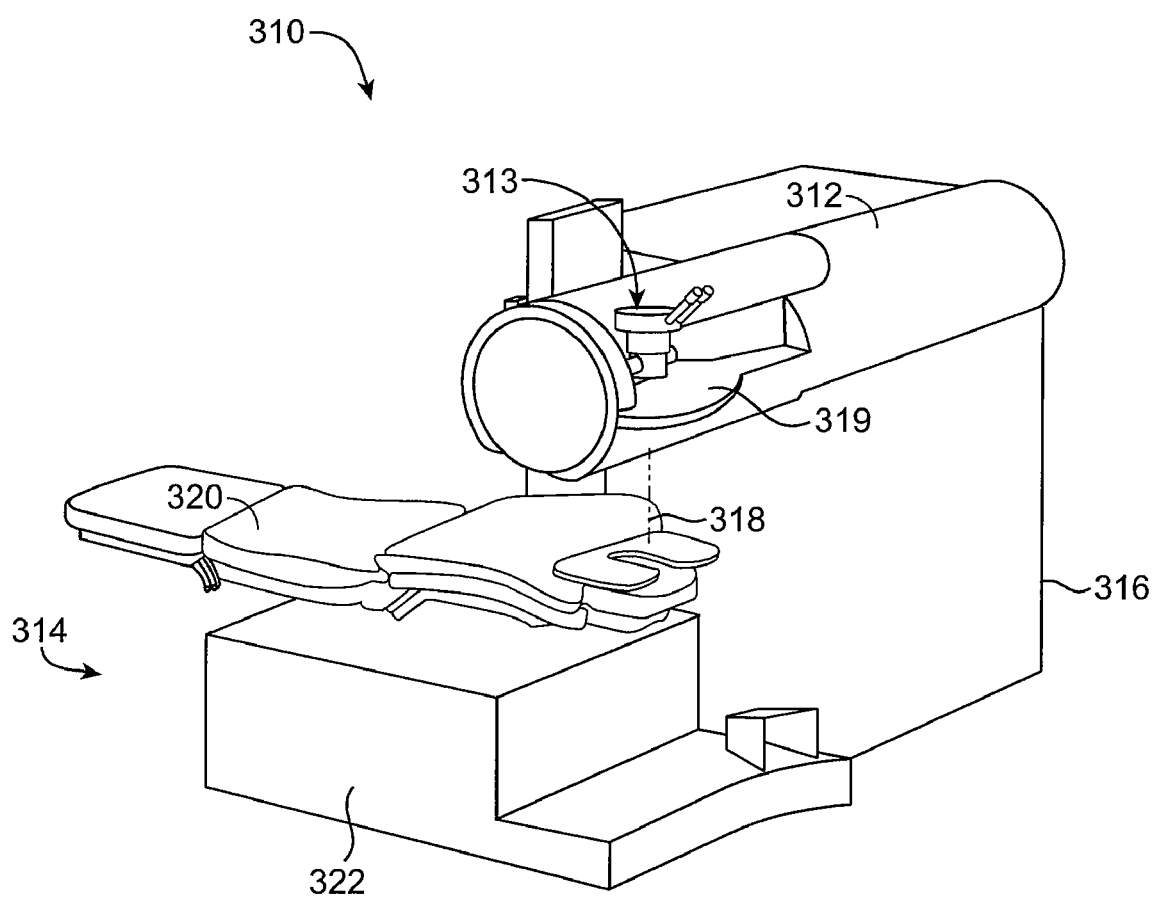
FIG. 3A is a perspective view schematically illustrating a laser eye surgery system having a patient support.
Figure 3B:
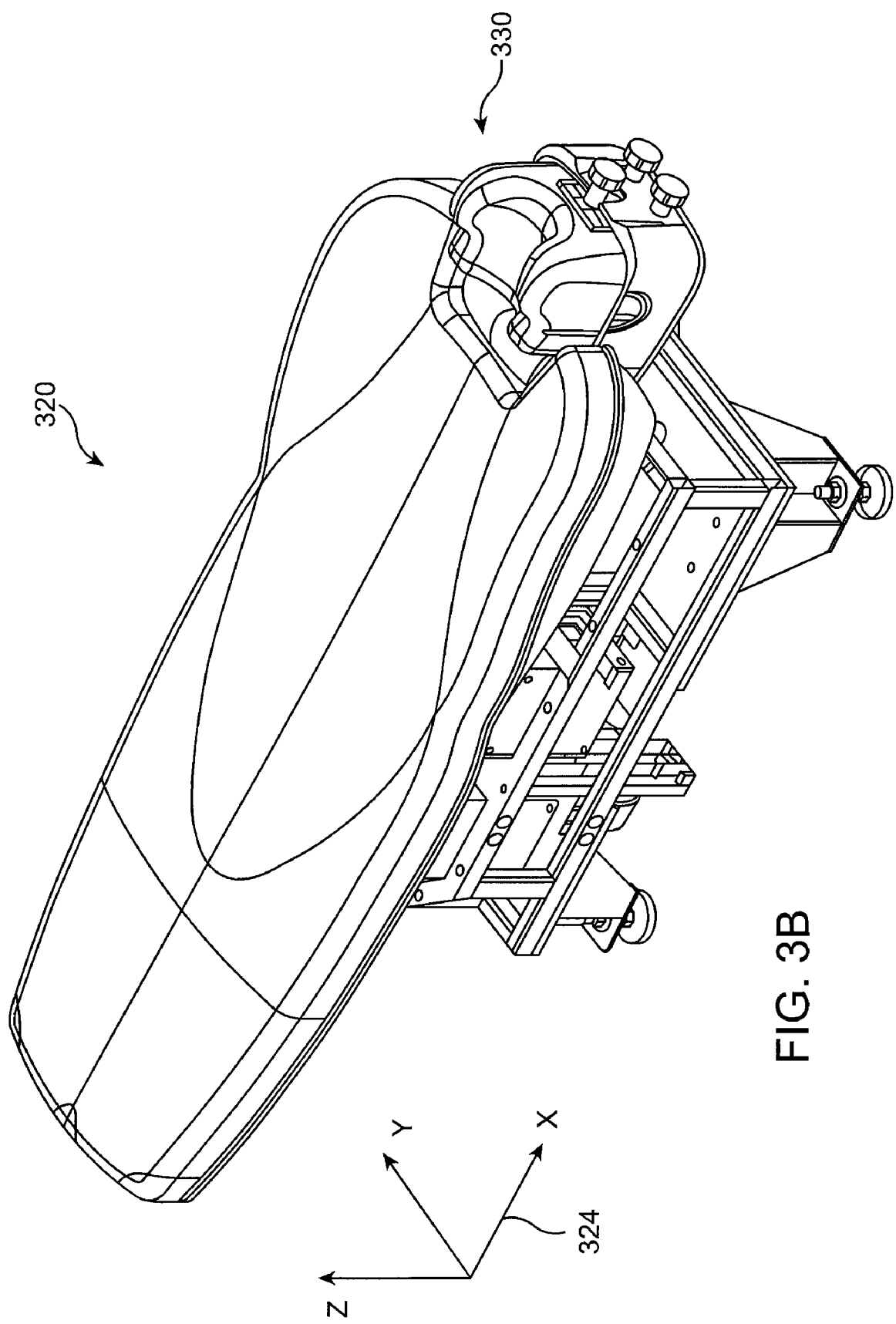
FIG. 3B is a perspective view of a patient support for use in the laser eye surgery system of FIG. 3A, in which the patient support has a headrest and neck rest which move vertically, and a compressive head pillow which restrains movement of the head during laser eye surgery, according to embodiments of the present invention.

Referring now to FIGS. 3A and 3B, an exemplary laser eye surgery system 310 generally includes a laser system 312 and a patient positioning system 314. Laser system 312 includes a housing 316 that includes both a laser and system processor. The laser generates a laser beam 318 which is directed to a patient's eye for the processor under the direction of a system operator. Delivery optics used to direct the laser beam, the microscope mounted to the delivery optics, and the like may employ existing structures from commercially available laser systems, including at least some portions of the STAR S4 ACTIVE TRAK™ excimer laser system and other laser systems available from Advanced Medical Optics, Inc. of Santa Ana, Calif. In some embodiments, laser eye surgery system 310 can move the patient support to align the patient with the laser system. Laser delivery system 310 may include optical components and an eye tracker to steer the laser beam in response to patient movement.

The system operator interface for laser system 312 may include an input device 319 which can be used to help align laser beam 318 in relation to an eye of a patient P. A microscope 313 can be used to image a cornea of the eye. Microscope 313 comprises an image sensor that captures images of the eye and is connected to a processor as described above. The user interface optionally including a joy stick (or any of a variety of alternative input components such as a track ball, touch screens, or any of a wide variety of alternative pointing devices). Input to the processor of laser system 312 may also be provided with a keypad, data transmission links such as an Ethernet, an intranet, the Internet, a modem, wireless devices, or the like. The user input can be used to adjust the position of the chair. In some embodiments, the patient will be automatically positioned with translational motion in three dimensions by the processor using images from the microscope image sensor.

In addition to (or in some cases, instead of) adjustments to the delivery optics directing laser beam 318, alignment between the patient and the laser treatment may be provided at least in part by patient positioning system 314. Patient positioning system 314 generally includes a patient chair 320, a patient support movement mechanism 322, the image sensor of microscope 313 and the processor. Patient chair 320 may be contoured, helping to position the patient at a nominal location on the patient support such that the patient support defines nominal optical axes near the locations of the patient's left and right eyes. Patient chair 320 may comprise a bed, patient seat, or reclining patient seat. Movement mechanism 322 may allow patient chair 320 to move clear of the laser system 312 to facilitate loading and unloading of the patient onto the patient support, and may move the patient support quickly to a nominal left or right eye treatment position in which the nominal optical axes defined by the patient support are aligned with laser beam 318. Fine adjustments of the position of patient chair 320 may then be effected using fine motion control of movement mechanism 322 so as to more accurately align the patient with the laser system, as more fully described in U.S. patent application Ser. No. 10/226, 867, filed Aug. 20, 2002, the full disclosure of which is incorporated herein by reference. In preferred embodiments, patient char 320 provides patient movement along three dimensions of a chair coordinate reference 324. As shown in FIG. 3B, chair 320 provides horizontal movement along an XY plane of chair coordinate reference 324 and vertical motion along a Z dimension of chair coordinate reference 324. Vertical motion along dimension Z of coordinate reference 324 is normal and at a 90 degree angle to the XY plane in preferred embodiments. In other embodiments, motion of the chair is at another angle to the XY plane.

The laser of laser system 312 will often comprise an excimer laser, ideally comprising an argon-fluoride laser producing pulses of laser light having a wavelength of approximately 193 nm. Each pulse of laser beam 318 preferably removes a microscopic layer of tissue, with the processor of laser system 312 scanning the pulses and/or profiling the pulses transmitted towards the patient's eye according to a pattern of pulses so as to resculpt the patient's cornea. Alternative laser or other electromagnetic radiation forms might also be used, particularly those well-suited for controllably ablating or reshaping corneal tissue without causing significant damage to adjacent and/or underlying tissues of the eye. Such laser systems may include solid state lasers, including frequency multiplied solid state lasers such as flash-lamp and diode pumped solid state lasers. Exemplary solid state lasers include UV solid state lasers having wavelengths of approximately 193-215 nm such as those described in U.S. Pat. Nos. 5,144,630 and 5,742,626. Other lasers that may be used with embodiments disclosed herein may include infrared lasers and ultrafast pulsed lasers, such as femtosecond lasers.

In addition to lateral alignment between the patient and delivery optics of laser system 312, patient chair 320 may also be used to help vertically position the patient (and more specifically, the eye of the patient) at a desired treatment location along the axis of laser beam 318. Such vertical adjustment of the patient or patient's eye can facilitate accurate ablation, imaging of the eye with the microscope of laser system 312, tracking movements of the eye so as to maintain alignment between laser beam 318 and the eye, and the like. In addition to providing vertical alignment, patient chair 320 may also be used to orient the face and eye of the patient with the delivery optics and laser beam 318. While the patient will often be viewing a fixation target incorporated into the laser delivery optics of laser system 312 so as to help maintain the eye at the proper orientation relative to the therapeutic laser beam, having the patient's head at an appropriate orientation may facilitate access to the corneal tissue free from interference from the upper or lower eyelids, and the like. Proper orientation of the head may also make it easier for the patient to maintain viewing fixation on the fixation target.

Referring again to FIGS. 3A and 3B, patient chair 320 can be seen in more detail in accordance with preferred embodiments. In some embodiments, the patient support may be articulated, optionally having a hinge or the like allowing the patient's legs or feet to be lowered independently of the torso. In some embodiments, a head support and/or restraint mechanism 330 may be provided. In some embodiments, the position of head pad 330 relative to the other portions of patient chair 320 may be moved, often by articulating one or more linkages. Exemplary head supports are more fully described in U.S. patent application Ser. No. 11/335,177, filed on Jan. 18, 2006, the full disclosure of which has been previously incorporated herein by reference.

Figure 3C:
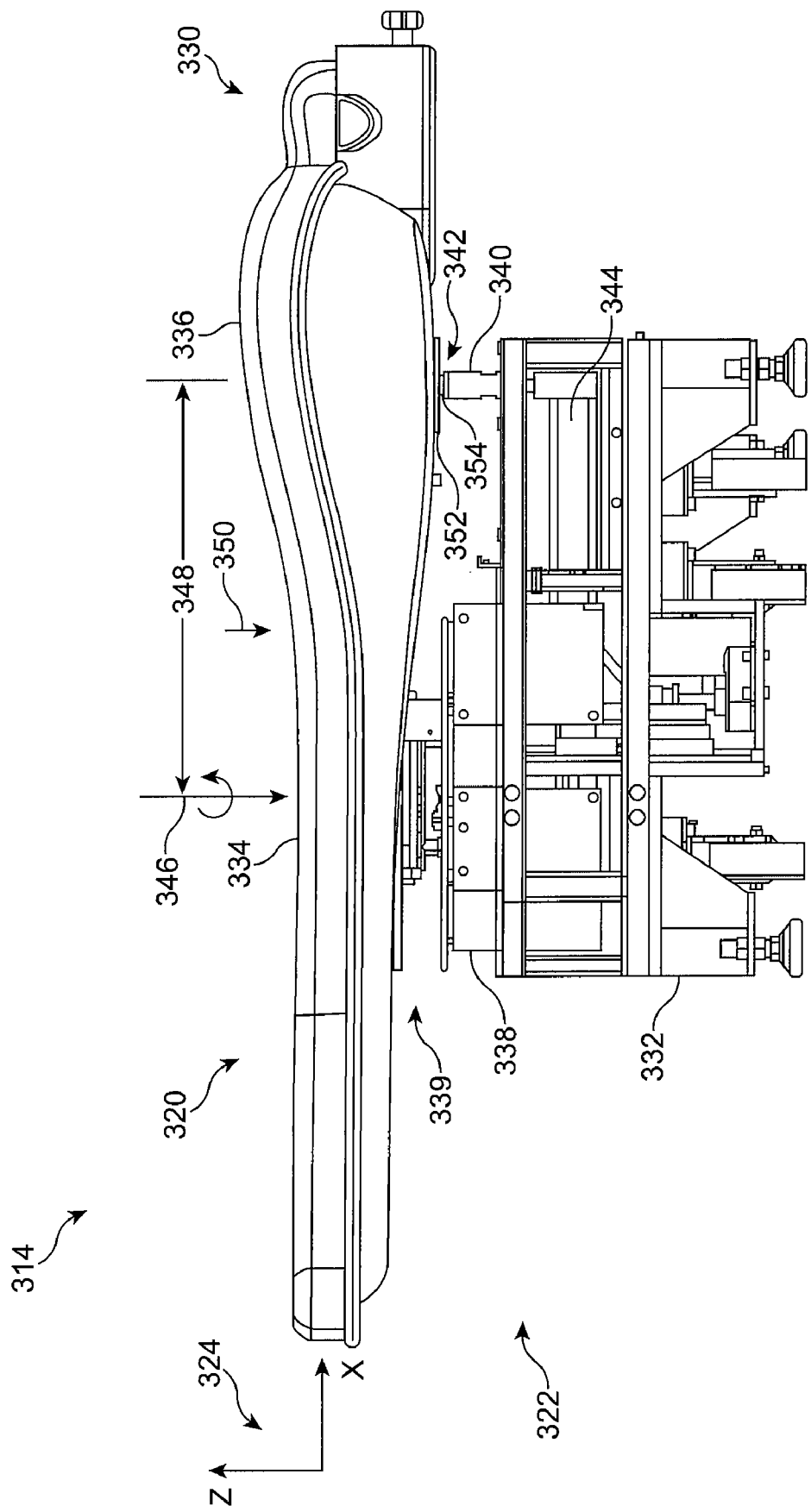
FIG. 3C. is a plan view of a patient support as in FIG. 3B having a stabilizing support, in accordance with embodiments of the present invention.
Figure 3D:
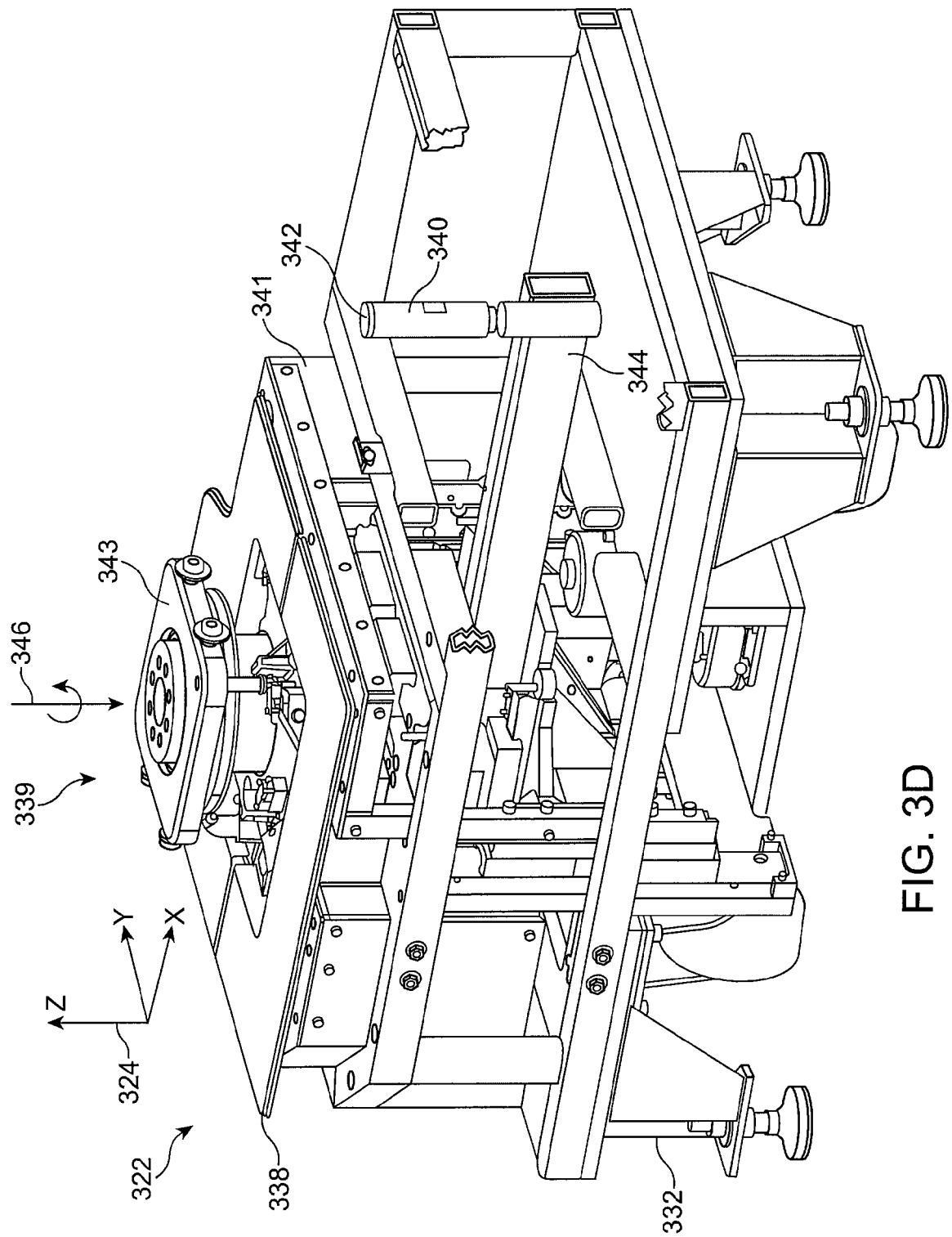
FIG. 3D is a perspective view of a movement mechanism, linkage and stabilizing member, in accordance with embodiments of the present invention, with portions of a frame removed for clarity.

Referring now to FIGS. 3C and 3D, patient positioning system 314 can be seen in more detail. An exemplary patient positioning system is described in U.S. patent application Ser. No. 11/342,278, filed on Jan. 27, 2006, entitled "Chair Stabilizer for Refractive Surgery", the full disclosure of which is incorporated herein by reference. Patient positioning system 314 generally includes a patient support such as a chair 320, a base 332, patient positioning mechanism 322 and a support member such as arm 340. Base 332 supports patient chair 320 and patient positioning mechanism 322. Patient positioning mechanism 322 connects patient chair 320 with base 332. Patient positioning mechanism 322 generally includes a linkage 338, often having joints and/or motors to accommodate or provide movement of patient chair 320 in relation to laser beam 318. Support arm 340 generally provides additional support to patient chair 320. Support arm 340 can be mounted to either base 332 or positioning mechanism 322.

The patient chair generally comprises a chair, seat or bed or similar structure for supporting a patient in a seated, reclined or supine position. Chair 320 generally includes head pad 330 which supports the head of the patient. Chair 320 is generally attached to linkage 338 at attachment locus 339, and a first portion such as hip portion 334 of chair 320, which is adjacent to the attachment locus. Hip portion 334 is supported at attachment locus 339 by linkage 338 so as to allow chair 320 to rotate about base 332 with an axis of rotation 346 passing through base 332. Axis 346 is located near and often passes through hip portion 334 of patient chair 320. Chair 320 generally pivots or rotates about axis 346 to permit loading and unloading of the patient. By swinging head pad 330 and an upper portion of chair 320 out from under laser system 312, the patient can be more easily loaded onto chair 320. After the patient has reclined in chair 320, the chair is then rotated about axis 346 to position the head of the patient and patient head pad 330 under laser system 312. Exemplary supports are commercially available from Advanced Medical Optics, Inc (formerly VISX, Inc.) of Santa Clara, Calif.

Chair 320 can be contoured to receive the patient. Contouring of chair 320 can be designed to receive a nominal patient having a nominal center of gravity 350. In many instances, nominal center of gravity 350 (and/or the actual center of gravity of the patient) is not coincident with attachment locus 339, resulting in cantilever effects.

In some embodiments, a chair stabilizer may be used to reduce or eliminate cantilever effects, as described in U.S. patent application Ser. No. 11/342,278, filed on Jan. 27, 2006, and entitled "Chair Stabilizer for Refractive Surgery," the full disclosure of which is incorporated herein by reference. Providing support to a second portion of chair 320 such as shoulder portion 336 can reduce or eliminate cantilever effects. The second portion of chair 320 is often located toward head pad 330 from the nominal center of gravity 350, in exemplary embodiments being disposed adjacent a nominal, chest, shoulder, neck, or head portion of the chair. Shoulder portion 336 can be located on chair 320 such that providing additional support to this location will reduce cantilever effects. The nominal center of gravity is often located between hip portion 334 and shoulder portion 336 of chair 320. Nominal center of gravity 350 of the patient is also often positioned between load bearing surface 342 and axis of rotation 346. This location of the nominal patient center of gravity between the supported portions 334 and 336 may result in decreased cantilever loading at attachment locus 339 and linkage 338, thereby improving stability of patient chair 320 and reducing patient motion.

Patient positioning mechanism 322 generally includes linkage 338 and provides rotation of the patient support about axis of rotation 346. Mechanism 322 and base 332 may generally comprise a pedestal. In some embodiments, base 332 is positioned beneath hip portion 334 and shoulder portion 336 of patient chair 320. Linkage 338 movably supports the patient chair, and often provides controlled motion of the patient chair in response to user input from input device 319. Linkage 338 can be attached to hip portion 334 of chair 320 at attachment locus 339. The patient chair is movable along a horizontal XY plane transverse to laser beam 318. In some embodiments, linkage 338 includes a horizontal XY motion stage 343 and a vertical Z motion stage 341. Base 332 can support vertical Z motion stage 341, and vertical Z motion stage 341 can be mounted to base 332. Vertical Z motion stage 341 may move linkage 338 vertically along dimension Z normal to the horizontal XY plane in a direction generally parallel to the laser beam. Horizontal XY motion stage 343 can be mounted to vertical Z motion stage 341. In these embodiments, vertical Z motion stage 341 can support horizontal XY motion stage 343, attachment locus 339 and hip portion 334 of the patient support. Vertical motion stage 341 can simultaneously move both XY motion stage 343, attachment locus 339, and hip portion 334 of the patient support in a vertical Z direction normal to the horizontal XY plane. Horizontal XY motion stage 343 can move attachment locus 339 and hip portion 334 of patient chair 320 along X and Y axes in the horizontal XY plane, which is generally perpendicular and/or transverse to laser beam 318. Three dimensional motion can be effected by combined motion of the vertical Z motion stage and the horizontal XY motion stage. As patient chair 320 is often rigid, support and motion of the hip portion of the patient support will generally effect support and motion of the entire patient support.

Figure 4:
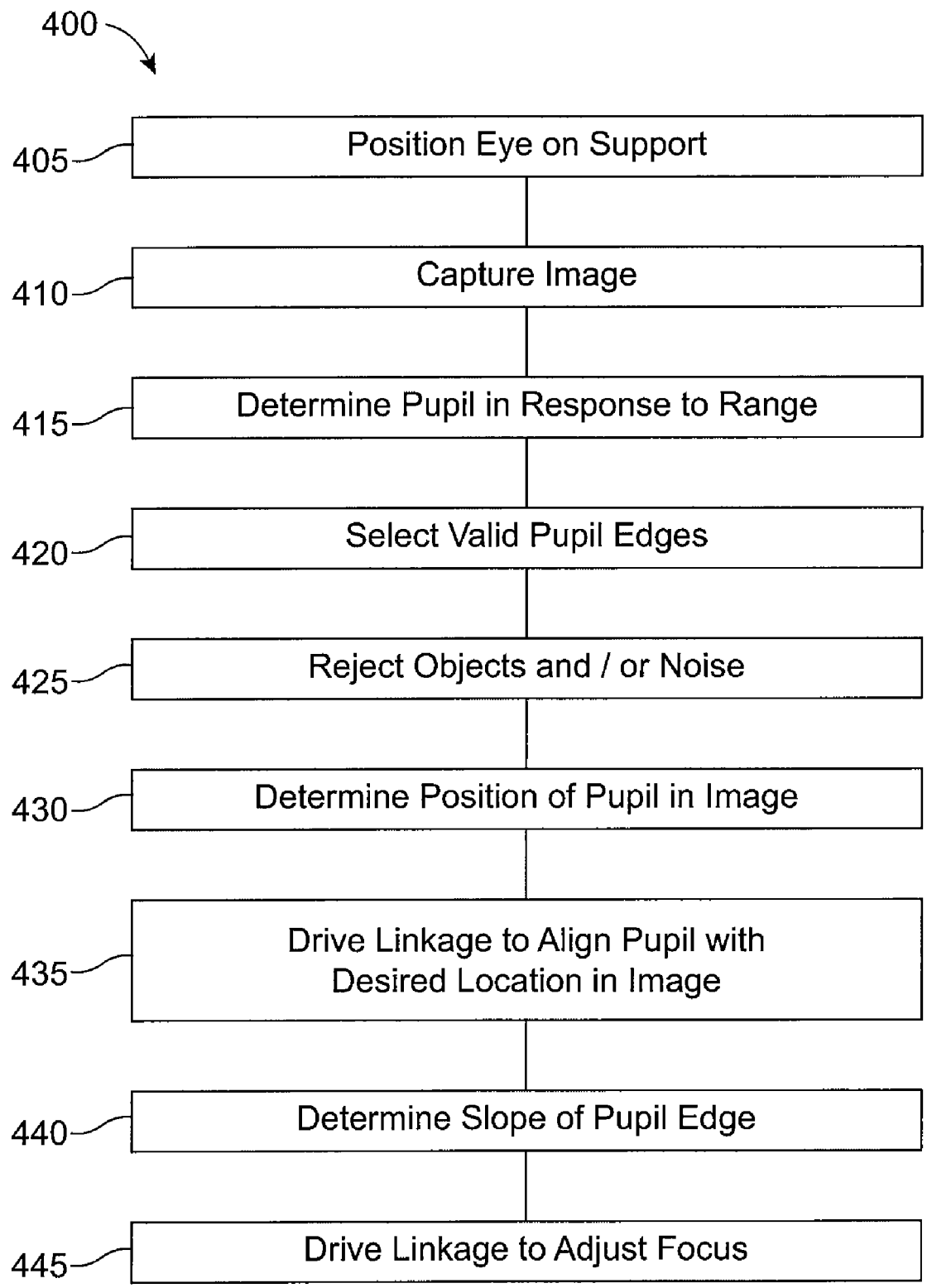
FIG. 4 shows a method of aligning an eye with a system image using a pupil threshold range of the image, according to embodiments of the present invention.

Referring now to FIG. 4 a method 400 is shown of aligning an eye in real-time with a system image using a pupil threshold range of the image, according to embodiments of the present invention. A step 405 positions an eye on a support. A step 410 captures an image of the eye. A step 415 determines an area of the pupil in response to a range. A step 420 selects valid pupil edges. In some embodiments, the validity of the pupil edges can be determined by connectivity of pixels within the pupil area such that the pupil area is continuous with a well defined boundary. A step 425 rejects objects and/or noise in response to the validity of the pupil edges. In some embodiments, the edges of the pupil can be smoothed and fit with curves and/or interpolated. A step 430 determines the position of the pupil in the image. The position of the pupil can be determined in response to the edge of the pupil and/or the centroid of the pupil area. A step 435 drives the linkage to align the pupil with a desired location in the image. In some embodiments, the desired location in the image comprises a pre-determined location in the image that corresponds to the optical axis of the instrument. A step 440 determines a slope of the pupil edge. The slope of the pupil edge can be determined in response to a width of the pupil edge, a change in intensity at the pupil edge and/or a gradient peak at the pupil edge. A step 445 drives the linkage so as to adjust a focus of the pupil and maximize the slope at the edge of the pupil. In some embodiments, the focus at the image sensor corresponds to alignment of the instrument with the eye. Steps 410 to 445 can be repeated and completed in real-time so as to automate alignment of the eye in real-time and maintain alignment with the eye while the eye moves. An additional step can confirm that the pupil is centered by repeating the imaging and calculation steps in real-time.

It should be appreciated that the specific steps illustrated in FIG. 4 provide a particular method of aligning an instrument with an eye, according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
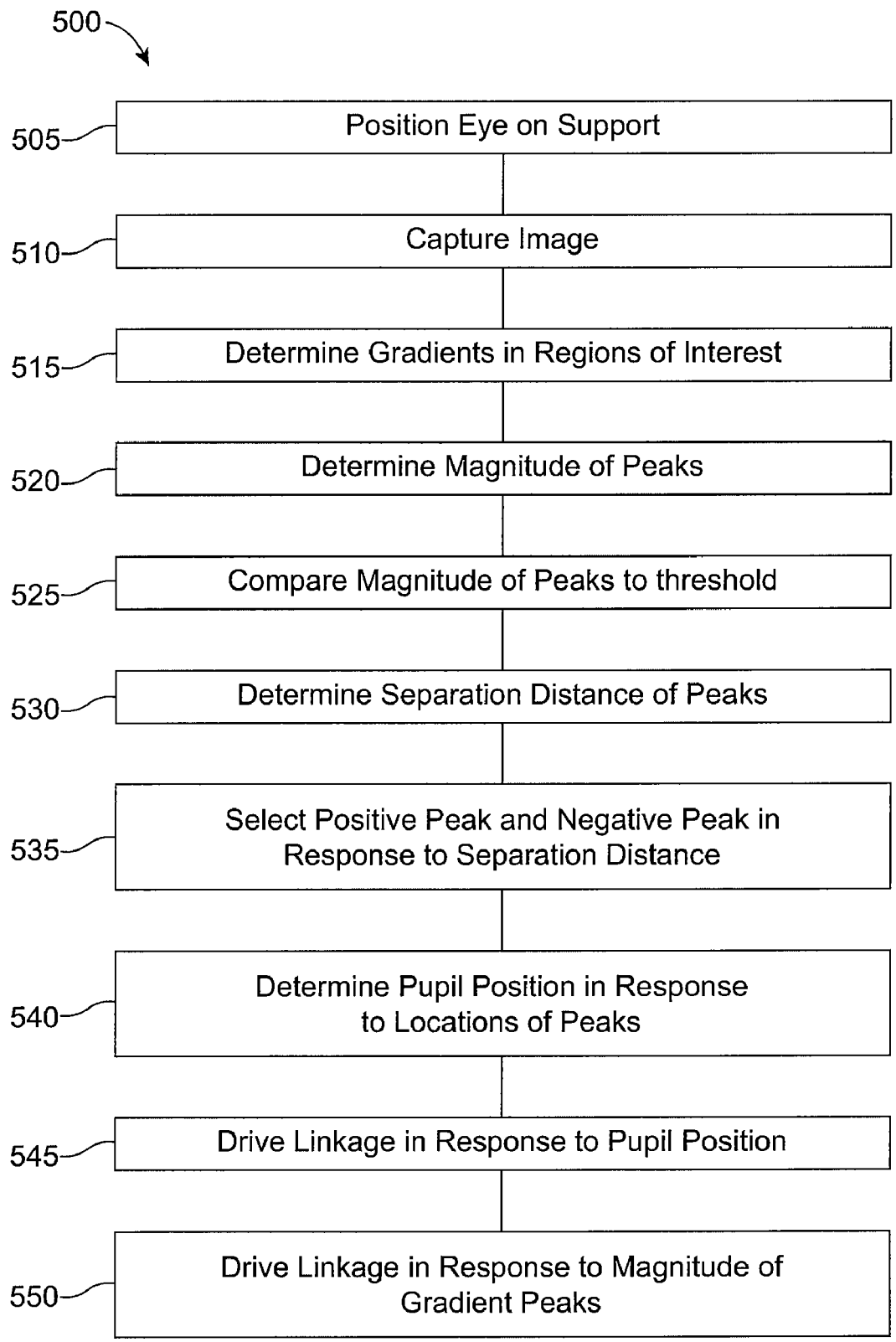
FIG. 5 shows a method of aligning an eye with a system using gradients of an optical tissue structure image, according to embodiments of the present invention.

Referring now to FIG. 5, a method 500 is shown of aligning an eye in real-time with a system using gradients of an optical tissue structure image, according to embodiments of the present invention. A step 505 positions an eye on a support. A step 510 captures an image of the eye. A step 515 determines gradients of intensity levels of the image for selected regions of interest, for example a horizontal row and a vertical column. A step 520 determines the magnitudes of gradient peaks in the image. As there may be both positive and negative peaks, the magnitude of the peak may correspond to the absolute value of the peak. A step 525 compares the magnitude of each peak to the threshold and selects peaks with magnitudes above the threshold. A step 530 determines a separation distance of the peaks. A step 535 selects a positive peak and a negative peak that correspond to edges of the pupil in response to the separation distance. In some embodiments, the positive and the negative peak of the pupil are separated by at least 2.5 mm and no more than 7.5 mm and the selected peaks have a separation distance within an expected range, for example from about 2.5 to 7.5 mm. A step 540 determines the position of the pupil in the image in response to the location of the peaks. In some embodiments, a horizontal position of the pupil in the image is located in between the positive horizontal gradient peak and the negative horizontal gradient peak, and the vertical position of the pupil is located in between the positive vertical gradient peak and the negative vertical gradient peak. A step 545 drives the linkage in response to the pupil position. In some embodiments, the linkage is driven in response to the location of the pupil in relation to a predetermined position of the image, for example the center of the image. To align the pupil with the predetermined position of the image, the linkage may be driven transverse to the optical axis. In some embodiments, the predetermined position of the image corresponds to alignment of the eye with the instrument. In some embodiments, the predetermined location in the image that corresponds to the desired location of the pupil in the image may be offset in relation to the center of the image. A step 550 drives the linkage in response to the magnitude of the gradient peaks. In some embodiments, the linkage is driven in response to a width of the gradient peaks. The linkage can be driven in response to the gradient peaks so as to adjust a separation distance from the image sensor to the eye.

It should be appreciated that the specific steps illustrated in FIG. 5 provide a particular method of aligning an instrument with an eye, according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A patient positioning system for use with a patient, the system comprising:
   a patient support to position the patient, the patient having an eye with a tissue structure;
   an optical image sensor to measure an optical image of the tissue structure;
   an optical train to optically couple the positioned eye to the sensor so as to form the image of the tissue structure on the sensor, wherein an optical path extends from the eye to the sensor; and
   a processor coupled to the optical image sensor to determine a gradient of an illumination level of the optical tissue structure image, the processor configured to adjust at least one of the optical train or the patient support in response to the gradient so as to focus the image on the sensor.

2. The device of claim 1 wherein the optical train comprises at least one lens or mirror, and the processors is configured to adjust the at least one lens or mirror to focus the image on the sensor.

3. The system of claim 1 wherein the illumination level comprises a grey scale level.

4. The system of claim 1 wherein the optical tissue structure image comprises a positive edge with a positive slope having a positive slope peak along the positive slope and a negative edge with a negative slope having a negative slope peak along the negative edge.

5. The system of claim 4 wherein the processor is configured to determine a distance from the positive edge to the negative edge of the tissue structure image.

6. The system of claim 5 wherein the processor is configured to determine the distance from the positive edge to the negative edge with the positive slope peak and the negative slope peak.

7. The system of claim 5 wherein the processor is configured to reject at least one of the positive edge or the negative edge in response to the distance from the positive edge to the negative edge.

8. The system of claim 5 wherein the processor is configured to reject at least one of the positive edge or the negative edge in response to the distance from the positive edge to the negative edge less than about 2.5 mm.

9. The system of claim 5 wherein the processor is configured to smooth a portion of the tissue structure image in response to the distance from the positive edge to the negative edge.

10. The system of claim 4 wherein the processor is configured to compare a magnitude of the positive slope peak to a threshold value and use the positive slope peak to determine the gradient and location of the positive edge of the tissue structure image when the magnitude of the positive peak is above the threshold value.

11. The system of claim 4 wherein the processor is configured to compare a magnitude of the negative slope peak to a threshold value and use the negative slope peak to determine the gradient and location of the negative edge of the tissue structure image when the magnitude of the negative peak is above the threshold value.

12. The device of claim 1 wherein the processor is configured to adjust the patient support in response to the gradient so as to change a separation distance from the patient to the image sensor.

13. A patient positioning system for use with a patient, the system comprising:
   an optical image sensor to measure an optical image of a tissue structure of an eye of the patient;
   an image sensor support to support the image sensor;
   a patient support to support the patient;
   a linkage to couple to the image sensor support with the patient support; and a processor coupled to the optical image sensor to determine a gradient of an illumination level of the optical tissue structure image, the processor coupled to the linkage and configured to articulate the linkage so as to adjust a separation distance from the tissue structure to the image sensor in response to the gradient of the optical tissue structure image.

14. The system of claim 13 wherein the processor is configured to increase the gradient of the tissue structure image with the separation distance from the tissue structure to the image sensor.

15. The system of claim 13 wherein the processor is configured to determine a lateral location of the tissue structure in the image and to move the linkage laterally to position the tissue structure in response to the location of the tissue structure in the image.

16. The system of claim 15 wherein the processor is configured to determine the gradient of the tissue structure and the location of the tissue structure from the same image.

17. The system of claim 15 wherein the processor is configured to move the linkage to adjust the separation distance and the lateral location of the tissue structure at the same time.

18. The system of claim 13 wherein an optical axis extends between the tissue structure and the image sensor and the separation distance extends along the optical axis.

19. The system of claim 13 wherein the tissue structure of the optical image comprises an iris with a pupil.

20. The system of claim 13 further comprising an imaging lens to form an image of the tissue structure of the eye on the image sensor, wherein the imaging lens is connected to the image sensor at a constant separation distance from the image sensor.

21. The system of claim 13 wherein the gradient comprises a first gradient along a first dimension of a first region of the tissue structure image and the processor is configured to determine a second gradient along a second dimension of a second region of the tissue structure image, wherein the processor is configured to adjust a separation distance from the tissue structure to the image sensor in response to the first gradient and the second gradient of the tissue structure image.

22. The system of claim 21 wherein the first dimension is substantially perpendicular to the second dimension.

23. The system of claim 13 wherein the linkage is adapted to move the image sensor support in response to the gradient of the tissue structure image.

24. The system of claim 23 further comprising an imaging lens to form an image of the tissue structure of the eye on the image sensor, wherein the imaging lens is connected to the image sensor to move with the image sensor at a constant separation distance from the image sensor.

25. The system of claim 13 wherein the linkage moves the patient support to adjust the separation distance in response to the gradient of the tissue structure image.

26. A patient positioning system for aligning an instrument with an eye of a patient, the system comprising:
an optical image sensor to capture an optical image of an iris of the eye of the patient, the iris comprising a pupil, the optical image comprising pixels with intensity levels;
an image sensor support to support the image sensor;
a patient support to support the patient;
a linkage to couple to the image sensor support with the patient support; and
a processor coupled to the optical image sensor to determine a pupil area of the image in response to intensity levels of the pixels within a range, the processor configured to determine slopes of the pixel intensity levels at the edge of the pupil, the processor coupled to the linkage and configured to articulate the linkage so as to adjust a separation distance from the tissue structure to the image sensor in response to the slopes of the pixel intensity levels at the edge of the pupil.

27. The system of claim 26 wherein the processor is configured to determine the slope with a width of the edge.

28. The system of claim 26 wherein the processor is configured to determine a location of the pupil area in the image.

29. The system of claim 26 wherein the range comprises a lower limit above zero and an upper limit that corresponds to estimated background levels of the pupil.

30. A method of aligning an instrument with an eye of a patient, the method comprising:
capturing an image of a tissue structure of the eye with an image sensor, the structure comprising an edge, the image comprising pixels with illumination levels;
determining a gradient of the tissue structure in response to the illumination levels of the pixels; and
adjusting an optical path from the tissue structure to the image sensor in response to the gradient of the tissue structure.

31. The system of claim 30 wherein the optical path is adjusted with movement of at least one lens or mirror along the optical path.

32. The system of claim 30 wherein the optical path is adjusted with at least one electro-optical lens or electro-optical mirror along the optical path.

33. The system of claim 30 wherein the optical path is adjusted with movement of a patient support.

34. The system of claim 30 wherein the tissue structure comprises an iris with a pupil and the processor is configured to determine a location of the pupil in the image.

35. A method of aligning an instrument with an eye of a patient, the method comprising:
capturing an image of an iris of the eye with an image sensor, the iris comprising a pupil, the image comprising pixels with intensity levels;
determining an area of the pupil in response to the intensity levels of the pixels within a range;
determining slopes of the intensity levels at an edge of the pupil near the pupil area; and
adjusting an optical path from the iris to the image sensor in response to the slopes to increase the slopes at the edge of the pupil.

36. The method of claim 35 wherein the separation distance is adjusted to increase peak values of the slopes.

* * * * *

UNITED STATES PATENT AND TRADEMARK OFFICE
CERTIFICATE OF CORRECTION

PATENT NO. : 7,575,322 B2
APPLICATION NO. : 11/747582
DATED : August 18, 2009
INVENTOR(S) : Seema Somani It is certified that error appears in the above-identified patent and that said Letters Patent is hereby corrected as shown below:

In the Claims

Column 18, lines 13-16, Claim 2 should read
2. The system of claim 1 wherein the optical train comprises at least one lens or mirror, and the processors is configured to adjust the at least one lens or mirror to focus the image on the sensor.

Column 18, lines 56-59, Claim 12 should read
12. The system of claim 1 wherein the processor is configured to adjust the patient support in response to the gradient so as to change a separation distance from the patient to the image sensor.

Column 20, lines 32-34, Claim 31 should read
31. The method of claim 30 wherein the optical path is adjusted with movement of at least one lens or mirror along the optical path.

Column 20, lines 35-37, Claim 32 should read
32. The method of claim 30 wherein the optical path is adjusted with at least one electro-optical lens or electro-optical mirror along the optical path.

Column 20, lines 38-39, Claim 33 should read
33. The method of claim 30 wherein the optical path is adjusted with movement of a patient support.

Column 20, lines 40-42, Claim 34 should read
34. The method of claim 30 wherein the tissue structure comprises an iris with a pupil and the processor is configured to determine a location of the pupil in the image.

Signed and Sealed this
Eleventh Day of February, 2014

Michelle K. Lee
*Deputy Director of the United States Patent and Trademark Office*